United States Patent [19]

Van Iten

[11] Patent Number: 5,545,157

[45] Date of Patent: Aug. 13, 1996

[54] PANTY SHIELD

[75] Inventor: Thomas P. Van Iten, Neenah, Wis.

[73] Assignee: Kimberly-Clark Corporation, Neenah, Wis.

[21] Appl. No.: 432,753

[22] Filed: May 2, 1995

Related U.S. Application Data

[62] Division of Ser. No. 230,938, Apr. 20, 1994.

[51] Int. Cl.⁶ .............................. A61F 13/15; A44B 1/04; A41D 27/12
[52] U.S. Cl. .................. 604/385.1; 604/387; 24/303; 2/46
[58] Field of Search ................. 604/385.1–402; 24/303; 2/46

[56] References Cited

U.S. PATENT DOCUMENTS

| | | | |
|---|---|---|---|
| 2,787,271 | 4/1957 | Clark | 128/290 |
| 2,807,263 | 9/1957 | Newton | 604/401 |
| 3,111,737 | 11/1963 | Heil | 24/201 |
| 3,161,932 | 12/1964 | Russell | 24/203 |
| 3,372,443 | 3/1968 | Daddona, Jr. | 24/201 |
| 3,888,255 | 6/1975 | Shah et al. | 128/290 R |
| 3,919,743 | 11/1975 | Cutler | 24/201 B |
| 4,249,267 | 2/1981 | Voss | 2/69 |
| 4,399,595 | 8/1983 | Yoon et al. | 24/201 B |
| 4,589,876 | 5/1986 | Van Tilburg | 604/385 R |
| 4,608,047 | 8/1986 | Mattingly | 604/387 |
| 4,710,979 | 12/1987 | Bull et al. | 2/48 |
| 4,746,494 | 4/1988 | Marchesi | 24/303 |
| 4,779,314 | 10/1988 | Aoki | 24/303 |
| 4,846,828 | 7/1989 | Mendelsohn | 604/387 |
| 4,882,815 | 11/1989 | Nilsen | 24/303 |
| 4,900,320 | 2/1990 | McCoy | 604/387 |
| 4,917,697 | 4/1990 | Osborn, III et al. | 604/387 |
| 5,098,422 | 3/1992 | Davis et al. | 604/385.1 |
| 5,103,501 | 4/1992 | Meisels . | |
| 5,133,705 | 7/1992 | Nakanishield | 604/387 |
| 5,207,665 | 5/1993 | Davis et al. | 604/402 |
| 5,217,448 | 6/1993 | Glaug et al. | 604/397 |
| 5,221,275 | 6/1993 | Van Iten | 604/387 |
| 5,300,055 | 4/1994 | Buell | 604/385.2 |
| 5,330,461 | 7/1994 | Leeker | 604/387 |

FOREIGN PATENT DOCUMENTS

| | | | |
|---|---|---|---|
| 0446818A2 | 9/1991 | European Pat. Off. . | |
| 0511905 | 11/1992 | European Pat. Off. | 604/387 |
| 0595047 | 5/1994 | European Pat. Off. | 604/387 |
| 2492238 | 10/1980 | France . | |
| 3736254A1 | 5/1989 | Germany . | |
| 48-73497 | 9/1973 | Japan . | |
| 586322 | 11/1993 | Japan . | |
| 2045335 | 10/1980 | United Kingdom . | |

OTHER PUBLICATIONS

Japanese Publication No. 46-12554.
Japanese Publication No. 40-36391.
Nippon Bascon KK—The Second Skin—A New Napkin: Knight Star Code: 857-8499.

Primary Examiner—David H. Willse
Assistant Examiner—K. M. Reichle
Attorney, Agent, or Firm—Thomas J. Connelly

[57] ABSTRACT

A panty shield is disclosed having a magnet attachment mechanism. The panty shield includes a baffle having a body-facing surface and first and second longitudinal side edges. First and second appendages extend laterally outward from the first and second longitudinal side edges, respectively. Each of the first and second appendages has a sufficient length to be folded inward and overlap one another. The panty shield further includes a first magnet secured to the baffle and a second magnet secured to one of the appendages. The appendages are folded around the crotch portion of an undergarment such that the appendages overlap one another. In this position, the first and second magnets are superimposed and can hold the panty shield secure to the undergarment. An absorbent article can be releaseably attached to the panty shield.

10 Claims, 4 Drawing Sheets

PANTY SHIELD

"This is a divisional application of copending Application Ser. No. 08/230,938, filed on Apr. 20, 1994."

FIELD OF THE INVENTION

This invention relates to a panty shield having an attachment mechanism for attaching it to the crotch portion of an undergarment. More particularly, this invention relates to a panty shield having a magnetic attachment mechanism.

BACKGROUND OF THE INVENTION

Panty shields are devices which are designed to be attached to the crotch portion of an undergarment and can retain an absorbent article adjacent to the wearer's body. Typically, panty shields serve as a liquid-impermeable barrier between an absorbent article and the undergarment to prevent the undergarment from becoming soiled or stained with body fluid. When used with a sanitary napkin, the panty shield will prevent menstrual fluid, blood, urine and other body excretions from contacting and soiling the undergarment.

Until now, most panty shields have been releaseably attached to the crotch portion of an undergarment with a garment-attachment adhesive. The adhesive, while providing a secure attachment, exhibits some disadvantages. First, the adhesive has a tendency to leave a residue on the undergarment and after a number of applications, this build up can result in undesirable tactile properties and/or discoloration. Such discoloration may cause the user to eventually discard the undergarment before it would normally be discarded. Second, the adhesive can stick to the skin and cause discomfort. Third, even though adhesives are relatively inexpensive, a peel strip is required to be placed over the adhesive, prior to use, to protect it from becoming contaminated. The cost of the peel strip along with the extra cost of cutting, aligning and placing the peel strip over the adhesive increases the total cost of manufacturing the product. "Velcro" and other types of hook and loop fasteners have made an entry into the marketplace with respect to panty shields. Although generally being more expensive than adhesive, they do allow for fastening and unfastening multiple times before failure. However, their biggest drawback is that they require good hand dexterity in order to align and secure the hook and loop fasteners. There still remains a real need for an attachment mechanism which can be readily fastened and unfastened a plurality of times without requiring extraordinary hand dexterity.

Now a panty shield having a unique attachment mechanism has been invented which is inexpensive to manufacture and which is easy to use.

SUMMARY OF THE INVENTION

Briefly, this invention relates to a panty shield having a magnet attachment mechanism. The panty shield includes a baffle having a body-facing surface and first and second longitudinal side edges. First and second appendages extend laterally outward from the first and second longitudinal side edges, respectively. Each of the first and second appendages has a sufficient length to be folded inward and overlap one another. The panty shield further includes a first magnet secured to either the body-facing surface or the garment-facing surface of the baffle and a second magnet secured to one of the appendages. The appendages are folded around the crotch portion of an undergarment such that the appendages overlap one another. In this position, the first and second magnets are superimposed to hold the panty shield secure to the undergarment. An absorbent article can be releaseably attached to the panty shield.

The general object of this invention is to provide a panty shield as a means for attaching an absorbent article to the crotch portion of an undergarment. A more specific object of this invention is to provide a panty shield having a magnetic attachment mechanism.

Another object of this invention is to provide an inexpensive panty shield having a fastening mechanism which can be fastened and unfastened numerous times without minimizing the strength of the attachment mechanism.

A further object of this invention is to provide a panty shield formed from a closed cell foam and having at least two overlapping appendages which are secured together by magnets.

Still another object of this invention is to provide a panty shield which is relatively simple to manufacture.

Still further, an object of this invention is to provide a panty shield with an inexpensive attachment mechanism.

Other objects and advantages of the present invention will become more apparent to those skilled in the art in view of the following description and the accompanying drawings.

DETAILED DESCRIPTION OF THE PREFERRED EMBODIMENTS

Figure 1:
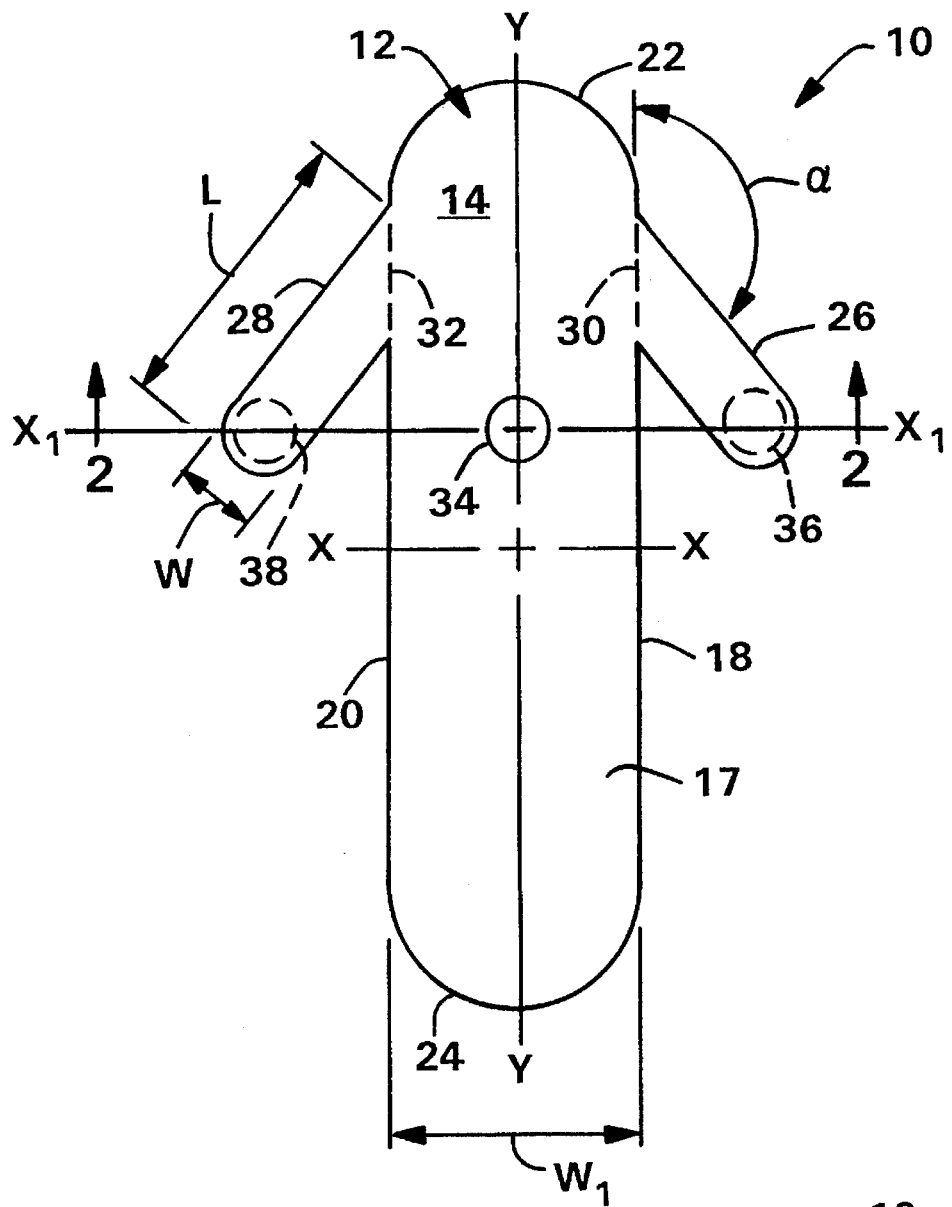
FIG. 1 is a top view of a panty shield having a magnet secured along it's central longitudinal axis and having first and second outwardly extending appendages with a magnet secured to each.
Figure 2:
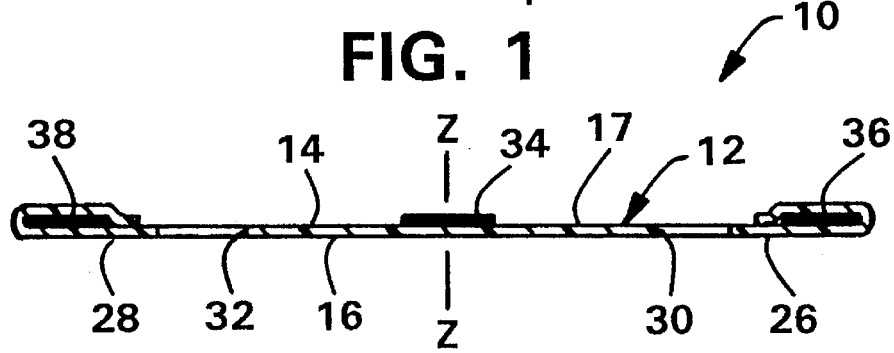
FIG. 2 is a cross-sectional view of the panty shield shown in FIG. 1 taken along line 2—2.

Referring to FIGS. 1 and 2, a panty shield 10 is shown which includes a baffle 12 having a body-facing surface 14, a garment-facing surface 16 and a central portion 17. The body-facing surface 14 is designed to be positioned facing the torso of a human body when the panty shield 10 is worn and the garment-facing surface 16 is designed to be positioned adjacent to an interior surface of the crotch portion of an undergarment. The central portion 17 of the baffle 12 is designed to cover the crotch portion of the undergarment.

The baffle 12 can be liquid-impermeable which will permit the passage of air and moisture vapor therethrough while blocking the passage of fluids or liquids therefrom. The baffle 16 could also be an air permeable micro-porous film which would prevent liquids from passing therethrough. The baffle 12 can be a foam, for example, a polyolefin foam or a polyurethane foam. A polyolefin foam can be made from polyethylene or polypropylene. The baffle 12 can be constructed of a liquid-permeable foam that has been treated or coated to made it liquid impermeable. For purposes of this invention, the baffle 12 is preferably a closed cell foam having a thickness in the range of about 0.2 mm to about 2.0 mm, preferably about 0.4 mm to about 1.6 mm, and more preferably, about 0.4 mm to about 0.8 mm. A closed cell foam tends to work best. Such a foam is sold under the trademark "Volara" and is distributed by Voltex, a division of Sekisui America Corporation, having an address at 100 Shepard Street, Lawrence, Mass. 01843. A closed cell foam having a thickness as specified above, has sufficient strength which allows it to be folded over upon itself without ripping or tearing.

The baffle 12 has first and second longitudinal side edges, 18 and 20 respectively which flank the central portion 17. The longitudinal side edges 18 and 20 can be linear or nonlinear and they can be aligned parallel or at an angle relative to one another. In FIG. 1, the longitudinal side edges 18 and 20 are linear and are aligned parallel to one another. The baffle 12 also contains a first end 22 and a second end 24. The first end 22 is spaced apart from and oppositely aligned with the second end 24.

The panty shield 10 further contains first and second appendages 26 and 28 which extend laterally outward from the longitudinal side edges, 18 and 20, respectively. The appendages 26 and 28 are shown as being integrally formed with the baffle 12 and have the same thickness as the central portion 17. However, the appendages 26 and 28 can be separate attachments to the central portion 17, if desired. The appendages 26 and 28 are shown as finger-like or ribbon-like members having a length L and a width W. When the panty shield 10 is a member having a width of about 2 to about 4 inches (about 51 mm to about 102 mm), the length of the appendages 26 and 28 should be such that they span across more than half of the width of the panty shield 10 and are capable of overlapping one another. In other words, when the appendages 26 and 28 are folded adjacent to the longitudinal side edges, 18 and 20, they should overlap one another and cross the longitudinal central axis Y—Y.

Figures 3, 4:
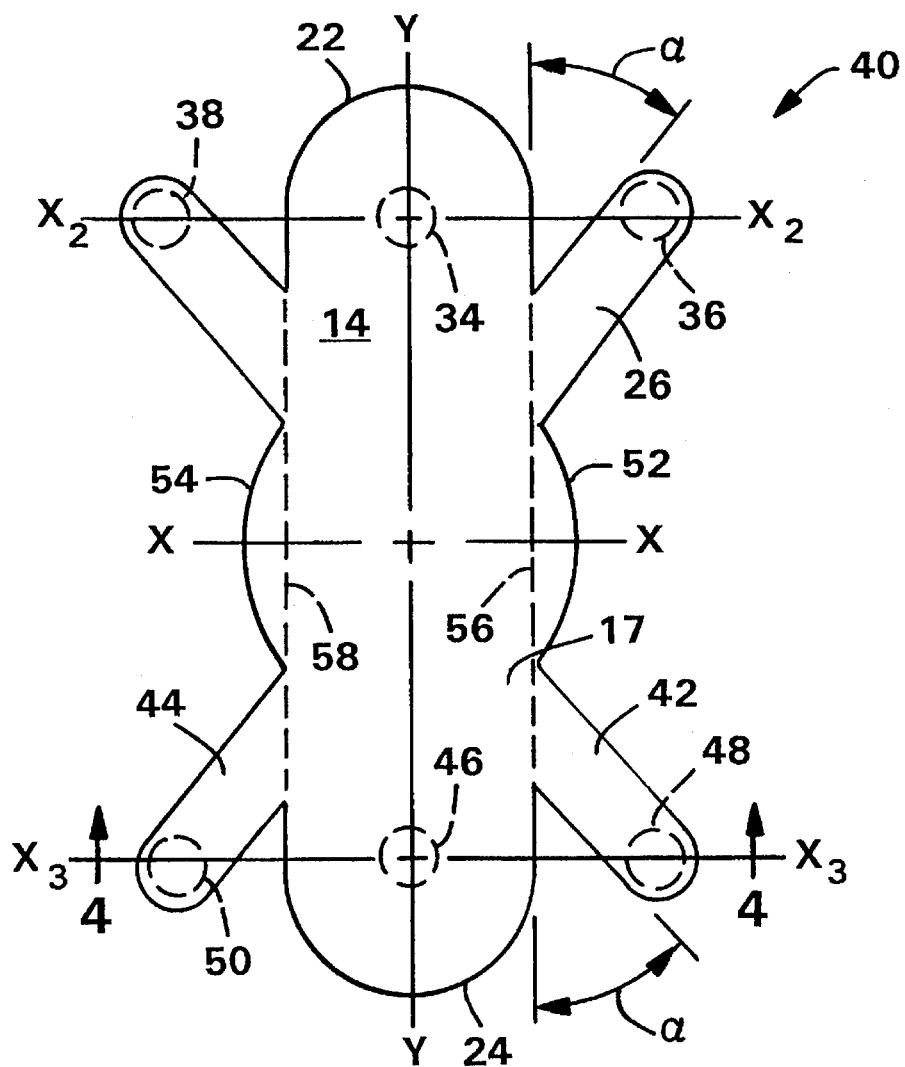
FIG. 3 is a top view of an alternative embodiment of a panty shield having a set of magnets secured along it's central longitudinal axis and having first and second pairs of outwardly extending appendages, and having a magnet secured to each appendage.
FIG. 4 is a cross-sectional view of the panty shield shown in FIG. 3 taken along line 4—4.

The width W of the appendages 26 and 28 can vary from between about 0.25 inches (about 6.35 mm) up to a width which would be approximately equal to the entire length of the panty shield 10. Preferably, the width W of each of the appendages 26 and 28 will be less than the width $W_1$ of the panty shield 10. More preferably, the width W will vary between about 0.25 inches to about 1.0 inches (about 6.35 mm and 25.4 mm), and most preferably, between about 0.5 inches to about 0.75 inches (about 0.72 mm to about 19.0 mm). Each of the appendages 26 and 28 are aligned at an angle alpha ($\alpha$) adjacent to the first or second ends, 22 and 24 respectively, and relative to the first and second longitudinal side edges, 18 and 20 respectively. The angle alpha ($\alpha$) can be an acute angle (less than 90 degrees) as shown in FIG. 3 or it can be an obtuse angle (greater than 90 degrees and less than 180 degrees) as is depicted in FIG. 1. When the appendages 26 and 28 are aligned at an acute angle, the angle should preferably be less than 60 degrees, and most preferably, should be between about 10 to about 50 degrees. When the appendages 26 and 28 are aligned at an obtuse angle, the angle should preferably be greater than about 100 degrees, and most preferably, should be between about 110 and about 170 degrees.

It has been found that when the appendages 26 and 28 are aligned at either an acute or an obtuse angle relative to longitudinal side edges, 18 and 20, they can be folded around the crotch portion of an undergarment very easily.. In the folded position, the appendages 26 and 28 will prevent longitudinal movement of the panty shield 10 relative to the undergarment. If the appendages 26 and 28 are aligned perpendicular (at 90 degrees) relative to the longitudinal side edges, 18 and 20 respectively, they will not be as successful in preventing longitudinal movement relative to the undergarment. The perpendicular alignment does prevent sideways or transverse movement of the panty shield 10 relative to the undergarment and could be used if desired.

The appendages 26 and 28 are a mirror image of one another when the panty shield 10 is divided along the longitudinal central axis Y——Y. It should be noted that the appendages 26 and 28 are shown as having the same length L and width W, although it is possible to make one longer or wider than the other if desired. The two appendages 26 and 28 are designed to be folded along fold lines 30 and 32, respectively, so that they can wrap around the outside edge of an undergarment and overlap the width of the crotch portion. The fold lines 30 and 32 can be imaginary lines on which the appendages 26 and 28 are folded or they can be actual hinges formed in a predetermined location on which the appendages 26 and 28 have to fold.

The panty shield 10 further includes attachment means for securing it to the crotch portion of an undergarment. The attachment means consist of a first member 34 and at least one other member 36. The first member 34 is secured to either the body-facing surface 14 or the garment-facing surface 16 of the baffle 12. Preferably, the first member 34 is secured to the body-facing surface 14. The first member 34 is preferably aligned close to or in alignment with the longitudinal central axis Y——Y. The first member 34 is offset from the transverse central axis X——X of the panty shield 10 although it could also be aligned therewith if desired. By offsetting the first member 34 from the transverse central axis X——X, one decreases the possibility that the wearer could feel the presence of it.

In FIGS. 1 and 2, the attachment means includes a second member 36 secured to the first appendage 26 and a third member 38 secured to the second appendage 28. Preferably, the second and third members, 36 and 38 respectively, are secured adjacent to or near the distal or free ends of the appendages, 26 and 28 respectively. The first, second and third members, 34, 36 and 38 can be magnets or some other type of device which can exert an attractive force when superimposed and aligned close to one another. The magnets provide an easy way for the user to reposition the panty shield 10 relative to the undergarment, should the need arise. One or more of the first, second and third members 34, 36 and 38, can consist of a permanent magnet while the other two members can be a receiver members having a magnetically susceptible metal engageable with the permanent magnet. The first attachment member 34 can be a fixed magnetic element while the second and third attachment members, 36 and 38 respectively, can be moveable magnetic elements. Likewise, each of the second and third attachment members 36 and 38 can be a fixed magnetic element while the first attachment member 34 is a moveable magnetic element.

When the first, second and third members, 34, 36 and 38 are magnets and/or receiver members, they should be wafer thin so the wearer of the panty shield 10 will not notice them. The magnets and the receiver members should have a thickness of less than about 0.25 inches (about 6.35 mm) and preferably less than about 0.12 inches (about 3.2 mm). A thickness of less than about 0.10 inches (about 2.54 mm) is most preferred. The magnets can be constructed of a neodymium-iron-boron material, a ceramic material or any other type of material having a ferrite base. The magnets and receiver members should have a holding force, when measured perpendicular to one another, of less than about 2.0 pounds, preferably less than about 1.0 pound, and most preferably, less than about 0.75 pounds. If the strength of the magnets and/or receiver members is too strong, it may be difficult for a person using the panty shield 10 to separate the attachment. If the strength of the magnets and/or receiver members is too weak, the attachment may not be adequate to secure the panty shield 10 to the crotch portion of an undergarment.

The first member 34 can be secured to either the body-facing surface 14 or the garment-facing surface 16 of the baffle 12 by an adhesive or by embedding the first member 34 into the foam baffle 12. It is also possible for the first member 34 to be secured to the baffle 12 by a mechanical fastener or some other type of bonding agent. When the first member 34 is secured to the garment-facing surface 16, it can be painted or coated to match the color of the baffle 12 so that it will be less noticeable to the user.

The second and third members, 36 and 38, can be secured near the free ends of the first and second appendages, 26 or 28, respectively. In FIGS. 1 and 2, the second member 36 is shown secured to the first appendage 26 and the third member 38 is secured to the second appendage 28. The first appendage 26 can have it's free or distal end folded over to enclose the second member 36 therebetween and the second appendage 28 can be folded in a similar fashion over the third member 38. It should be noted that the length of the first appendage 26 is preferably equal to the length as the second appendage 28. Different lengths appendages 26 and 28 can be used if desired. As with the first member 34, the second and third members 36 and 38 can be secured by an adhesive, be bonded in place by heat or pressure, or be secured by a mechanical means such as by sewing, stapling, etc.

In FIG. 2, the second and third members 36 and 38 are depicted as wafer thin magnets, each in the form of a circular disk. The magnets are positioned on the body-facing surface 14 of the baffle 12 and each has the free end of the first and second appendages, 26 and 28 respectively, folded over them.

Referring again to FIG. 1, the panty shield 10 is shown having a transverse central axis X——X and the first, second and third members, 34, 36 and 38 are shown aligned along a transverse axis $X_1$——$X_1$ which is spaced apart from the transverse central axis X——X. This configuration places the first and second appendages, 26 and 28 respectively, closer to the first end 22. It has been found that by placing the appendages 26 and 28 closer to an end of the panty shield 10, that the first, second and third members 34, 36 and 38 can be located away from the central transverse axis of the panty shield 10. By placing the first, second and third members 34, 36 and 38 closer to one of the ends 22 or 24, it has been found that the user will not notice the weight of the magnets as much as if they were in the center portion of the panty shield 10.

When the second member 36 is secured to the first appendage 26 and the first appendage 26 is folded on the fold line 30, it should vertically overlap the first member 34. This can be obtained when the first member 34 is situated at the intersection of the longitudinal axis Y——Y and the transverse axis $X_1$——$X_1$ and the second member 36 is secured to the first appendage 26 and is located along the transverse axis $X_1$——$X_1$. The third member 38 is secured to the second appendage 28 and when the second appendage 28 is folded on the fold line 32, it should vertically overlap the first member 34 in a similar fashion. This is possible by locating it along the transverse axis $X_1$——$X_1$. It should be noted that the first, second and third members, 34, 36 and 38 can be offset from the transverse axis $X_1$——$X_1$ but the size and shape of the first, second and third members, 34, 36 and 38 may have to be enlarged to assure an overlap. Such an offset will also depend on the angle at which the appendages 26 and 28 are folded and the orientation of the fold lines 30 and 32 relative to the longitudinal side edges 18 and 20. However, when the first, second and third members, 34, 36 and 38 are each in the form of a thin magnetic disk, having a diameter of about 0.5 to 1.0 inches (about 12.7 mm to 25.4 mm) or less, it is beneficial to arrange the first, second and third members 34, 36 and 38 such that they will substantially overlap one another (be superimposed) when the appendages 26 and 28 are folded inward. This will assure that adequate magnetic strength is present to provide a secure attachment.

It should also be noted that the magnets can vary in configuration and include circular disks, squares, rectangles or any other geometric shape. For manufacturing purposes, a circular disk works fine.

Referring to FIGS. 3 and 4, a panty shield 40 is shown which has a first pair of appendages 26 and 28 which are formed at an acute angle alpha (α) relative to the first end 22 and a second pair of appendages 42 and 44 which are formed at an acute angle alpha (α) relative to the second ends 24. If the panty shield 40 was folded on the central transverse axis X——X, the upper half would be a mirror image of the lower half. The first pair of appendages 26 and 28 contain attachment members 36 and 38 which are positioned adjacent to the first end 22 and aligned along a transverse axis $X_2$——$X_2$ which is spaced apart from the central transverse axis X——X. The panty shield 40 also contains three additional attachment members, 46, 48 and 50 which can also be magnets. The attachment members 46, 48 and 50 are positioned adjacent to the second end 24 and are aligned along a transverse axis $X_3$——$X_3$ which is spaced apart from the central transverse axis X——X. One attachment member 46 can be located at the intersection of the longitudinal axis Y——Y and the transverse axis $X_3X_3$. The other two attachment members 48 and 50 can be similar in all respects to the first and second members 36 and 38. The attachment member 48 is secured to the appendage 42 and the other attachment member 50 is secured to the appendage 44. It should be noted that the first and second sets of attachment members 34, 36 and 38, and 46, 48 and 50 respectively, can be identical or can differ depending upon the desires of the manufacturers.

A second difference exhibited in FIGS. 3 and 4 is that the panty shield 40 has nonlinear longitudinal side edges 52 and 54 located between the outward extending pairs of appendages 26 and 28, and 42 and 44, respectively. The nonlinear side edges 52 and 54 are convex, such that they extend laterally outward. The amount that the longitudinal side edges 52 and 54 extend outward can vary depending upon one's needs. The outwardly extending longitudinal side edges 52 and 54 are capable of folding along longitudinal axes, 56 and 58 respectively, as they contact the inner thighs of a woman who is wearing the panty shield 40. The side edges 52 and 54 serve to shield an undergarment from body fluid that may flow off the top surface of the absorbent article which can be releasably attached to the body-facing surface 14 of the panty shield 40.

Referring to FIG. 4, one will notice that the first and second sets of attachment members 34, 36 and 38 and 46, 48 and 50 respectively, are located on the garment-facing surface 16 of the baffle 12. This is a variation of FIG. 2 wherein they were located on the body-facing surface 14. This configuration can be obtained by securing the first attachment members 34 and 46 directly to the garment-facing surface 16 and by folding or wrapping the free or distal ends of the appendages 26 and 28 under the second and third attachment members, 36 and 38, respectively.

Figure 5:
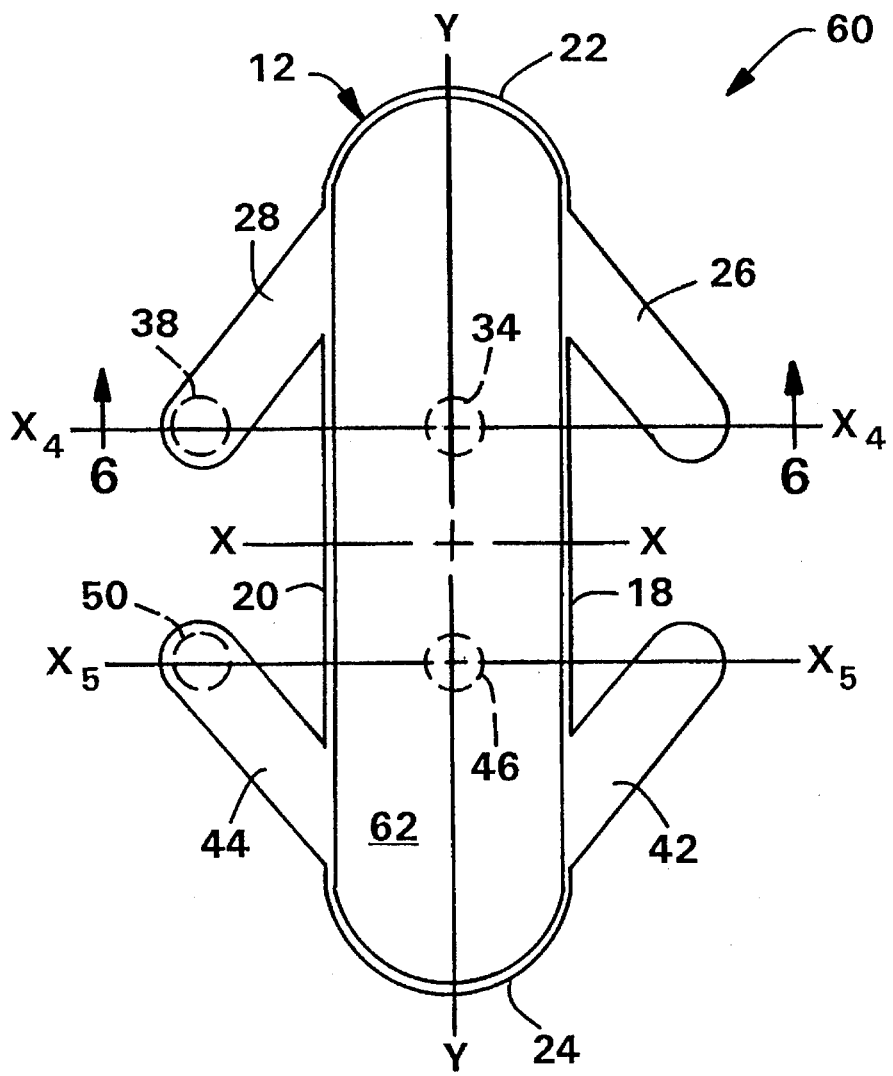
FIG. 5 is a top view of an alternative embodiment of a panty shield having a set of magnets secured along it's central longitudinal axis and having first and second pairs of outwardly extending appendages, and having a magnet secured to one appendage of each pair.
Figure 6:
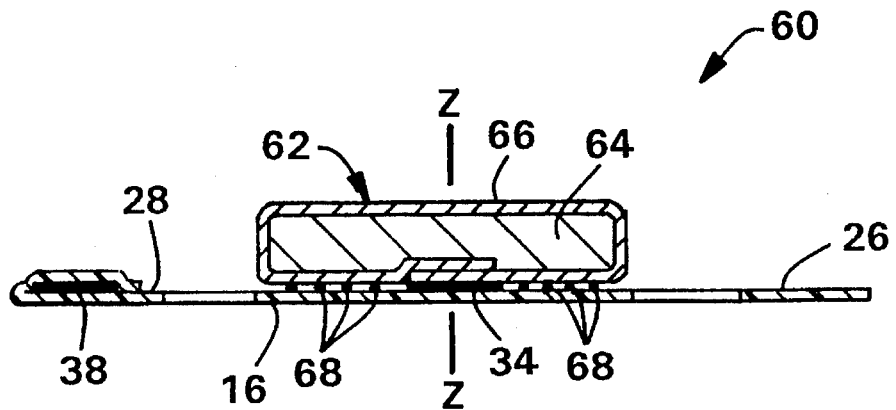
FIG. 6 is a cross-sectional view of the panty shield shown in FIG. 5 taken along line 6—6.

Referring to FIGS. 5 and 6, a top view of a panty shield 60 is shown which is similar to FIG. 3, except for a couple of differences. First, the first and second pairs of appendages are aligned at an obtuse angle alpha ($\alpha$) relative to the first and second ends, 22 and 24, respectively. Second, the first attachment members 34 and 46 are secured to the body-facing surface 14. Third, the two pairs of magnets 34 and 38, and 46 and 50 are aligned along transverse axes, $X_4$——$X_4$ and $X_5$——$X_5$ respectively. The transverse axes $X_4$——$X_4$ and $X_5$——$X_5$ are offset from the central transverse axis X——X. If the panty shield 60 was folded on the central transverse axis X——X, the upper half would be a mirror image of the lower half. Fourth, the panty shield 60 has straight or linear longitudinal side edges 18 and 20 as are depicted in FIG. 1. Fifth, the appendages 26 and 42 do not have an attachment member secured to them. The elimination of the two attachment members 36 and 48 will decrease the overall cost of the panty shield 60 and simplify the manufacturing process. It will also require that the appendages 26 and 42 be first folded over the magnets, 34 and 46 respectively, before the appendages 28 and 44 are folded over so that the magnets 38 and 50 will be attracted to the magnets, 34 and 46 respectively, and the appendages 26 and 42 will be sandwiched therebetween.

In FIGS. 5 and 6, the panty shield 60 is shown having an absorbent article 62 secured to it's body-facing surface 14. The absorbent article 62 can be a rectangular pad, such as a sanitary napkin, a panty liner, etc. which includes an absorbent 64 enclosed by a liquid-permeable cover 66. The absorbent article 62 can be releasably secured to the panty shield 60 by an adhesive 68. The adhesive 68 can be in the form of a single band, several longitudinally aligned strips or a plurality of independent dots. The absorbent article 62 is designed to be disposed of after use while the panty shield 60 is designed to be reused numerous times and can be cleaned if it becomes soiled by body fluid.

Figure 7:
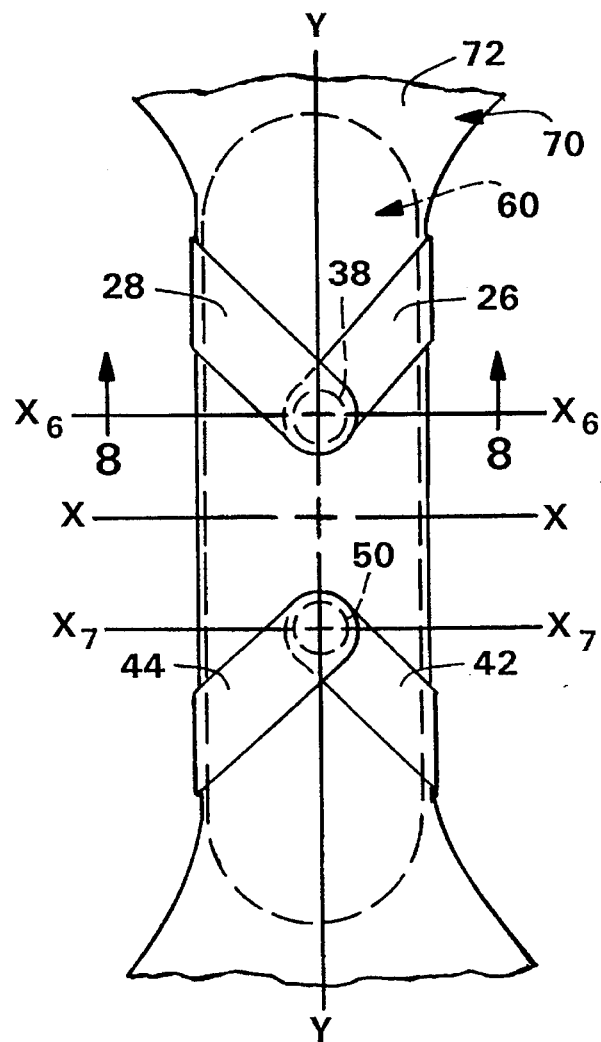
FIG. 7 is a bottom view of the panty shield depicted in FIG. 5 attached to the crotch portion of an undergarment.
Figure 8:
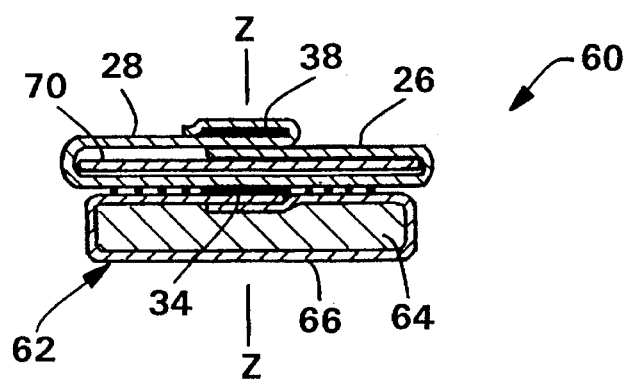
FIG. 8 is a cross-sectional view of the panty shield shown in FIG. 7 taken along line 8—8.

Referring to FIGS. 7 and 8, the panty shield 60 depicted in FIG. 5 is shown positioned in the crotch portion of an undergarment 70. The undergarment 70 has an exterior surface 72 around which is wrapped the first and second pairs of appendages 26 and 28, and 42 and 44. The two pairs of appendages 26 and 28, and 42 and 44 are folded around the crotch portion of the undergarment 70 and overlap such that the two pairs of magnets 34 and 38, and 46 and 50 will be vertically aligned or superimposed relative to one another. The two pairs of magnets 34 and 38, and 46 and 50 will overlap one another along the transverse axes, $X_6$——$X_6$ and $X_7$——$X_7$ respectively. In this position, the first appendage 26 (the one without the magnet) is first folded over the magnet 34 and then the second appendage 28 (containing the magnet 38) is folded over the first appendage 26. The first and second appendages, 26 and 28 respectively, overlay the first magnet 34 and the magnetic force of the magnets 34 and 38 will hold the panty shield 60 secure to the undergarment 70. Likewise, the third and fourth appendages, 42 and 44 respectively, are folded in a similar fashion such that the third appendage 42 is folded first against the exterior surface 72 of the undergarment 70 and then the fourth appendage 44 is folded over it. The magnet 46 is attracted to the magnet 50 and provides a secure attachment between the panty shield 60 and the undergarment 70.

The angular disposition of the appendages 26 and 28, and 42 and 44 prevent the panty shield 60 from moving longitudinally along the Y——Y axis with respect to the undergarment 70. When two pairs of appendages 26 and 28, and 42 and 44 are present, the panty shield 60 is more stable in that forward and backward sliding relative to the undergarment 70 is diminished. The acute or obtuse angle at which the appendages 26 and 28, and 42 and 44 are aligned relative to the longitudinal side edges 18 and 20 play a significant role in preventing longitudinal movement of the panty shield 10 with respect to the undergarment 70.

Referring to FIG. 8, the position of the folded appendages 26 and 28 are shown wherein the two attachment members 34 and 38 are superimposed relative to one another along a central Z——Z axis. In this position, the undergarment 70 is trapped therebetween and the panty shield 60 is held secure thereto.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

I claim:

1. A panty shield comprising:

a) a baffle having a central portion with first and second longitudinal side edges, and first and second appendages extending laterally outward from said first and second longitudinal side edges respectively, each of said first and second appendages having a sufficient length to be folded inward and overlap one another; and b) means for holding said panty shield to an undergarment, said means including a first attachment magnet designed to be superimposed relative to and mate with a second magnet when said first and second appendages are folded around the undergarment, said first magnet being secured to said central portion of said baffle by an adhesive and said second magnet being secured to one of said appendages.

2. The panty shield of claim 1 wherein said baffle is a closed cell polyolefin foam which is liquid-impermeable.

3. The panty shield of claim 2 wherein said foam has a thickness of between about 0.2 mm to 2.0 mm.

4. A panty shield comprising:

a) a liquid-impermeable baffle having a body-facing surface, a garment-facing surface, first and second longitudinal side edges and first and second appendages extending laterally outward from said first and second longitudinal side edges, respectively, each of said first and second appendages aligned at an acute angle relative to said longitudinal side edges and each having a sufficient length to be folded inward and overlap one another; and b) means for holding said panty shield to an undergarment, said means including a first attachment member positioned adjacent to said body-facing surface of said baffle and a second attachment member secured to one of said appendages, and said first attachment member designed to be superimposed relative to and mate with said second attachment member when said first and second appendages are folded around the undergarment.

5. The panty shield of claim 4 wherein said acute angle is less than 60 degrees.

6. The panty shield of claim 5 wherein said acute angle is between about 10 to about 50 degrees.

7. A panty shield comprising:

a) a liquid-impermeable baffle having a body-facing surface, a garment-facing surface, first and second longitudinal side edges, first and second spaced apart ends, and first and second pairs of appendages each including two members extending laterally outward from said first and second longitudinal side edges, respectively each pair of appendages positioned adjacent to said first and second ends, respectively, and aligned at an angle relative to said longitudinal side edges, and each member having a sufficient length to be folded inward and overlap said other member of said pair; and b) attachment means for securely holding said panty shield to an undergarment, said attachment means including two sets of magnets, a first magnet of each set secured to said baffle and a second magnet of each set secured to one member of each pair of appendages, said first set of magnets designed to be superimposed relative to and mate with said second magnet of each set of magnets when said first and second pairs of appendages are folded around said undergarment.

8. The panty shield of claim 7 wherein said magnets are made from a neodymium-iron-boron material.

9. The panty shield of claim 7 wherein said magnets are made from a ceramic material.

10. The panty shield of claim 7 wherein said first magnet of each set of said magnets is secured to said body-facing surface of said baffle.

* * * * *